(12) United States Patent
Picard et al.

(10) Patent No.: US 6,514,259 B2
(45) Date of Patent: Feb. 4, 2003

(54) PROBE AND ASSOCIATED SYSTEM AND METHOD FOR FACILITATING PLANAR OSTEOTOMY DURING ARTHOPLASTY

(75) Inventors: Frederic Picard, Pittsburgh, PA (US); Anthony M. DiGioia, III, Pittsburgh, PA (US); James E. Moody, Pittsburgh, PA (US); Branislav Jaramaz, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 6 days.

(21) Appl. No.: 09/776,497

(22) Filed: Feb. 2, 2001

(65) Prior Publication Data

US 2002/0107522 A1 Aug. 8, 2002

(51) Int. Cl.$^7$ .............................................. A61B 17/56
(52) U.S. Cl. .......................... 606/88; 606/87; 606/103
(58) Field of Search ........................... 606/130, 88, 87, 606/69–71, 79, 82; 600/414, 417, 426, 429; 703/11

(56) References Cited

U.S. PATENT DOCUMENTS

| 4,759,350 | A |   | 7/1988  | Dunn et al. |
| 5,251,127 | A |   | 10/1993 | Raab |
| 5,263,972 | A | * | 11/1993 | Evans et al. ................. 606/176 |
| 5,611,147 | A |   | 3/1997  | Raab |
| 5,728,099 | A | * | 3/1998  | Tellman et al. ................ 606/65 |
| 5,871,018 | A | * | 2/1999  | Delp ........................... 128/898 |
| 5,926,782 | A |   | 7/1999  | Raab |
| 6,002,859 | A |   | 12/1999 | DiGioia, III et al. |
| 6,161,080 | A | * | 12/2000 | Aouni-Ateshian et al. .... 703/11 |
| 6,179,836 | B1 |  | 1/2001  | Eggers et al. |
| 6,190,395 | B1 | * | 2/2001 | Williams ..................... 606/130 |

* cited by examiner

Primary Examiner—Kevin Shaver
Assistant Examiner—Michael B. Priddy
(74) Attorney, Agent, or Firm—Kirkpatrick & Lockhart LLP

(57) ABSTRACT

A plate probe and associated system and method for facilitating the orientation of an osteotomy and the implantation of an artificial joint component during arthroplastic surgery requiring an osteotomy. The probe comprises a coupler and a plate. The coupler is configured so that it can be connected to a position tracker, such that the position and orientation of the plate can be determined from the position of the tracker. The plate is configured so that it can be inserted into an opening of a bone-cutting mechanical guide, which is generally designed for receiving and guiding a surgical saw blade during a cutting operation.

20 Claims, 10 Drawing Sheets

PROBE AND ASSOCIATED SYSTEM AND METHOD FOR FACILITATING PLANAR OSTEOTOMY DURING ARTHOPLASTY

BACKGROUND OF THE INVENTION

1. Field of the Invention

The invention relates to computer-aided implantation of artificial joint components and, more particularly, to a plate probe and associated system and method used with a surgical navigation system during artificial joint implantation and associated operations that require osteotomy.

2. Description of the Invention Background

Currently, over 200,000 total hip replacement (THR) and over 250,000 total knee replacement (TKR) operations are performed annually in the United States alone. Many of these operations are repeat procedures to correct errors in alignment of the implant and the limb associated with the joint involved in the operation. Such errors lead to accelerated implant wear, early prosthesis loosening and sub-optimal clinical function. Although existing mechanical alignment guides have improved the precision of arthroplasty or joint replacement, errors in implant and limb alignment continue to occur.

Recently computer-assisted surgical systems and techniques have been developed to address the shortcomings of the purely mechanical surgical techniques. U.S. Pat. No. 6,002,859 discloses a computer-assisted system and method for facilitating the implantation of an artificial component in a joint. This system includes a computer, associated software and a tracking device. A computer model of the joint and a model of the artificial component are prepared pre-operatively. The tracking device collects positional data through point probes, i.e. probes that come in contact with a point. The tracking device determines the coordinates of the physical point, such as a point on the patient's body, with which the probe is placed in contact, thus creating a reference point. The system identifies the position of the component within the joint model. Using the data collected from the tracking device, the system aligns the joint model with the actual joint and the component model with the actual component.

During arthroplasty, damaged parts of joint bone must be removed and remodeled to allow a prosthetic component to fit in connection to the joint. It is desirable to accurately determine the orientation of planned planar cuts of the bones of a joint and to verify the orientation of the planar cut after the surgical cut has been performed. Determining such orientation by using a point probe or other mechanical alignment guides is an indirect procedure, which is still prone to error.

There remains, therefore, a need for an improved system and probe that can be used to measure and track the orientation of planar surfaces during computer-assisted surgical operations involved in arthroplasty.

SUMMARY OF THE INVENTION

The invention meets the identified needs, as well as other needs, as will be more fully understood following a review of this specification and drawings.

One embodiment of the invention discloses a probe for facilitating the orientation of an osteotomy, i.e. a bone cut. The probe comprises a coupler and a plate. The coupler is configured so that it can be connected to a position tracker, such that the position and orientation of the plate can be determined from the position of the tracker. The plate is configured so that it can be inserted into an opening of a guide which is generally designed for receiving and guiding a surgical saw blade during a cutting operation.

In another embodiment, the probe and a position tracker may be included in a system, which further includes a computer system comprising a pre-operative geometric planner and a pre-operative kinematic biomechanical simulator in communication with the preoperative geometric planner. The pre-operative kinematic biomechanical simulator outputs a position for implantation of the artificial component and a position and orientation of the osteotomy.

The invention also includes a method for facilitating the implantation of an artificial component during arthroplastic surgery that requires a planar osteotomy. The method includes creating a model of a joint and a model of an artificial component for implantation in the joint. The method further includes calculating a range of motion based on a simulated movement of the joint with the artificial component in a test position, determining the desired implant position based on the calculated range of motion and a predetermined range of motion and aligning the model of the joint with the joint and the model of the artificial component with the artificial component. The method also includes tracking the desired position of the artificial component and the joint, modeling the plane of the osteotomy, and tracking the plane of the osteotomy.

The invention also includes a method of facilitating a planar osteotomy on a joint during surgery. The method comprises positioning a bone-cutting guide on a portion of the joint prior to the osteotomy, attaching a probe having a planar portion to a position tracker and inserting the planar portion into an opening in the bone-cutting guide. The method also includes verifying and correcting the orientation of the plane of the osteotomy before performing the osteotomy, and may also include verifying the orientation of the plane of the osteotomy after performing the osteotomy.

Other features and advantages of the invention will become apparent from the detailed description of the embodiments set forth herein and from the appended claims.

DETAILED DESCRIPTION OF THE INVENTION

Figure 1A:
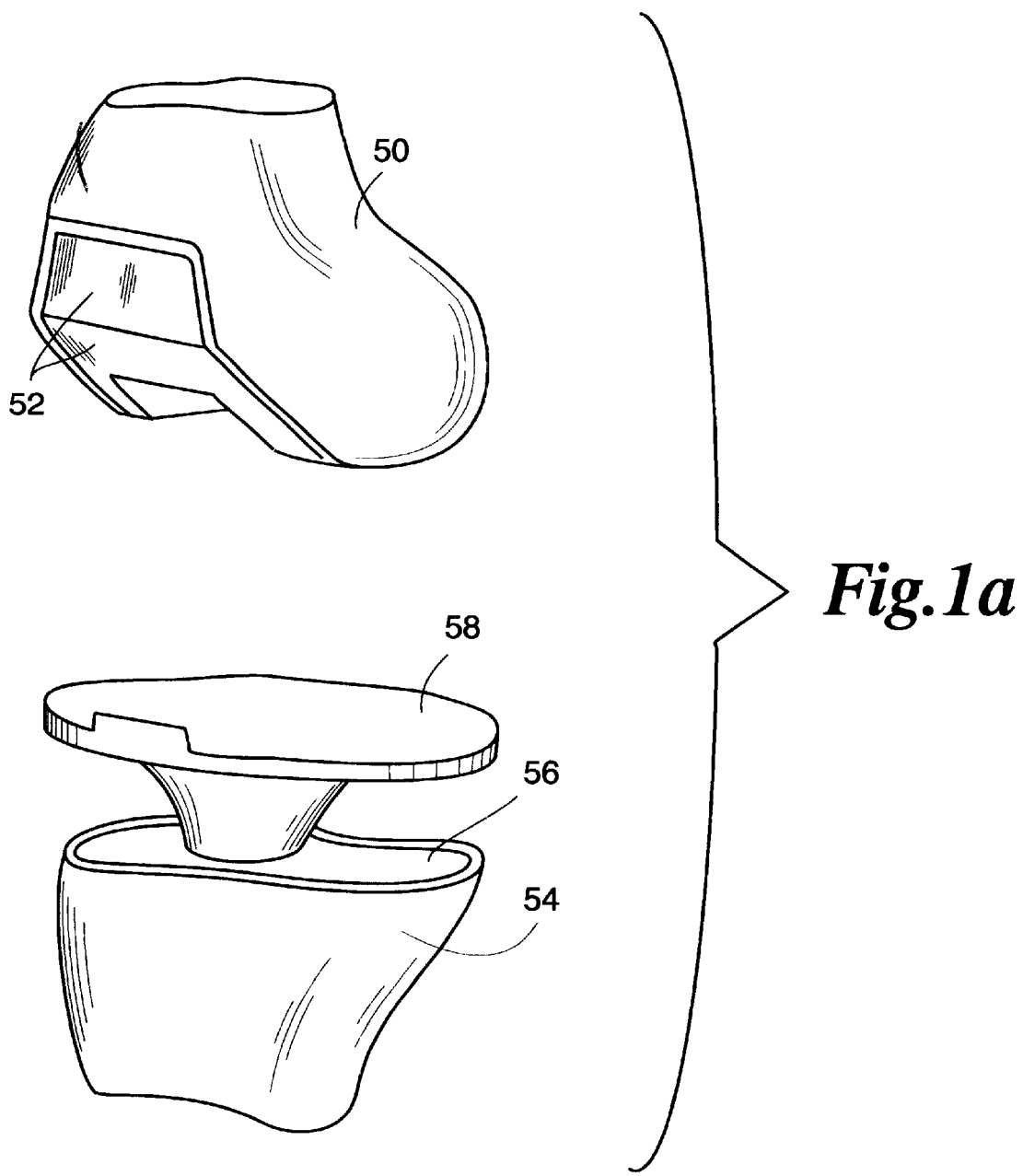
FIG. 1(a) is a schematic diagram showing in prespective view exemplary planar osteotomies and a prosthetic component in a knee replacement operation.
Figure 1B:
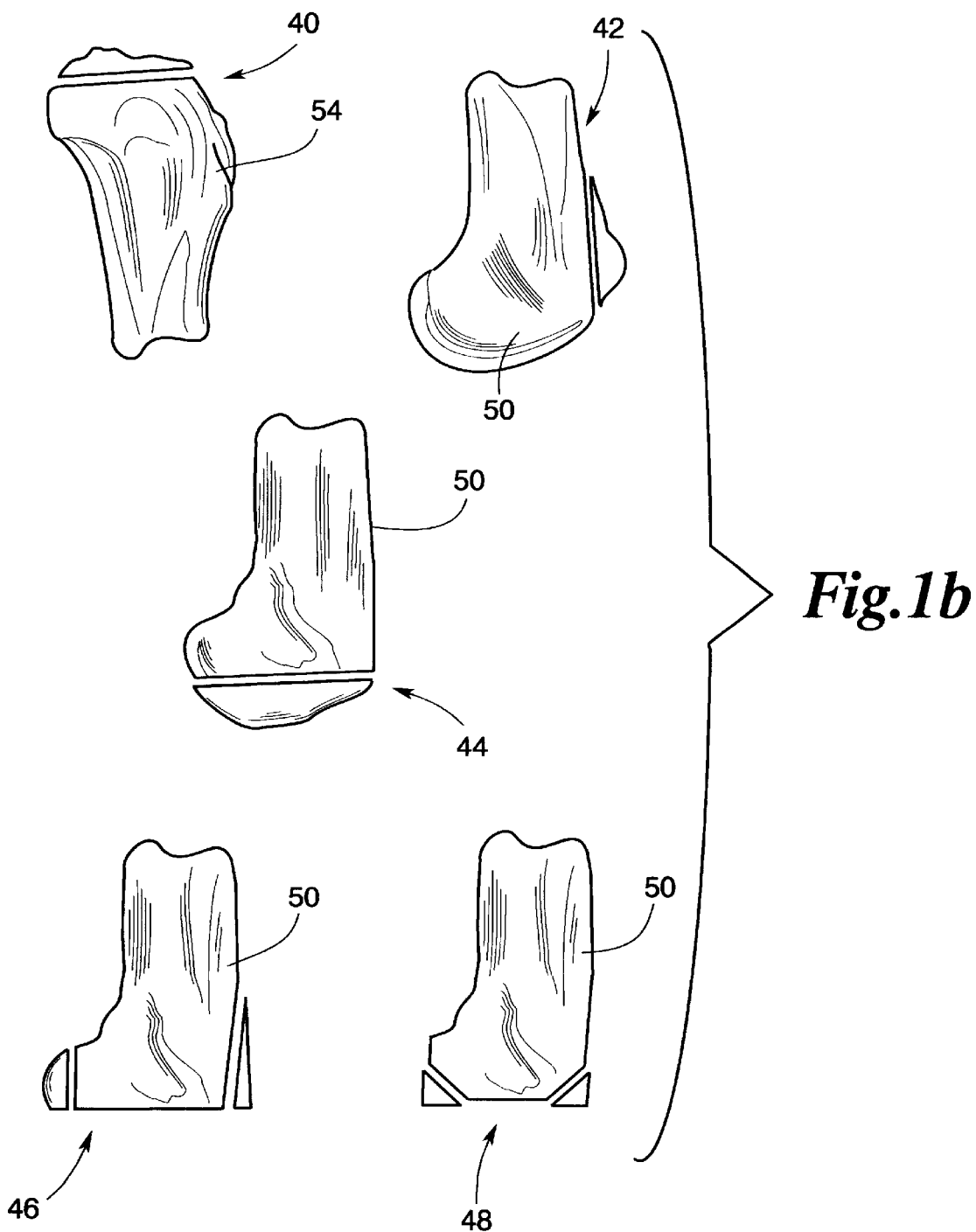
FIG. 1(b) is a schematic diagram showing a series of osteotomies for a total knee replacement operation

In the following description of the invention, reference is made to FIGS. 1–12(b). Although the present invention is described in terms of knee replacement or reconstruction, the person of ordinary skill in the art will appreciate that the invention is equally useful with replacement or reconstructive procedures for other joints, such as hip, shoulder, hand and wrist, foot and ankle, or elbow. In addition, while the embodiments disclosed herein are particularly well-suited for joint reconstruction, the skilled artisan will readily appreciate that the unique and novel features of these various embodiments could be easily adapted to a variety of different surgical operations that require bone cuts (osteotomies) along a planar surface. Accordingly, the protection afforded to the various embodiments disclosed and claimed herein should not be limited to surgical operations specifically adapted for joint reconstruction.

It is further to be understood that the Figures and descriptions of the present invention have been simplified to illustrate elements that are relevant to a clear understanding of the invention, while eliminating or, giving only cursory treatment of, other elements and/or descriptions thereof found in known systems and devices for arthroplasty and computer assisted surgery. A discussion of such elements, which are well known in the art and do not facilitate a better understanding of the present invention, is not provided herein.

Surgical operations for joints involving the implantation of an artificial component, or prosthesis, in the joint, typically require a number of planar cuts to remove damaged areas of cartilage and bone in the joint and reshape the bone to allow the artificial component to fit in the joint. In total knee replacement (TKR), for example, the femur 50 may be reshaped by several planar cuts 52, as shown schematically in FIG. 1. Similarly, the tibia 54 is also cut to create a planar surface 56, which receives a prosthetic tibial component 58. The femoral cuts 52, the tibial cut 58 and any other planar cuts that may be necessary during TKR, for example, must conform to a planned orientation for a close fit with the implant components. Any deviation, depending on its magnitude, may cause problems ranging from mild patient discomfort to extreme pain caused by significant malalignment, as well as failure of the component and repeat corrective surgery. U.S. Pat. No. 4,759,350 describes a system of instruments for reshaping the femur and tibia using planar cuts and details the associated surgical procedure for TKR. A series of planar cuts for TKR is shown in more detail in FIG. 1(b) and includes cuts of the proximal tibia 40, of the anterior femoral condyles 42, of the distal femur 44, the anterior and posterior condyles 46, and chamfer cuts 48.

Figure 4:
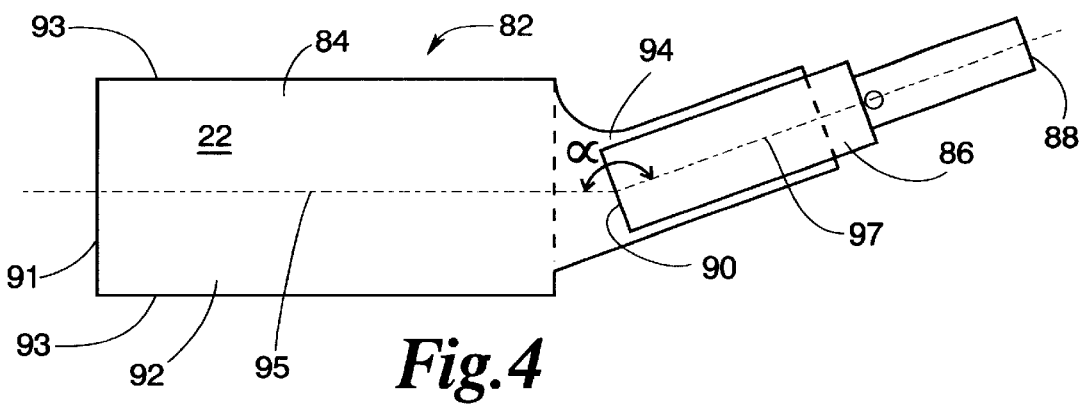
FIG. 4 is plan view of an embodiment of a plate probe according to the invention.
Figure 5A:
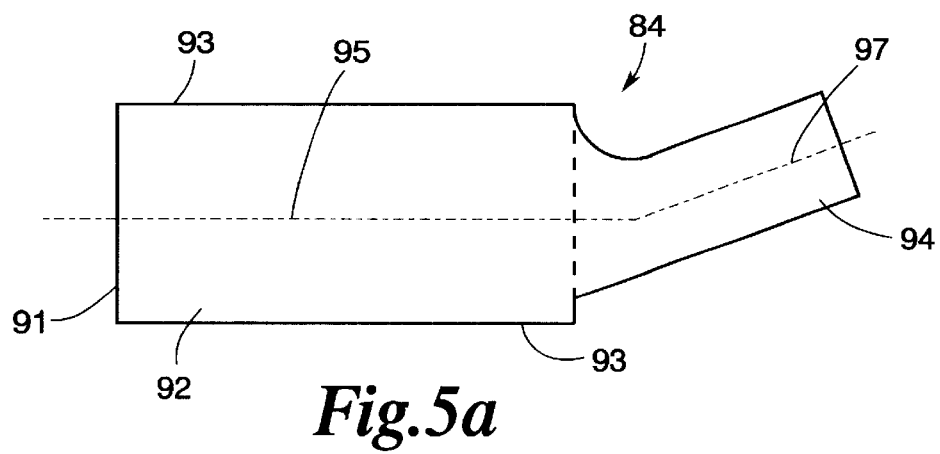
FIG. 5(a) is a plan view of the plate of the plate probe of FIG. 4.
Figure 5B:
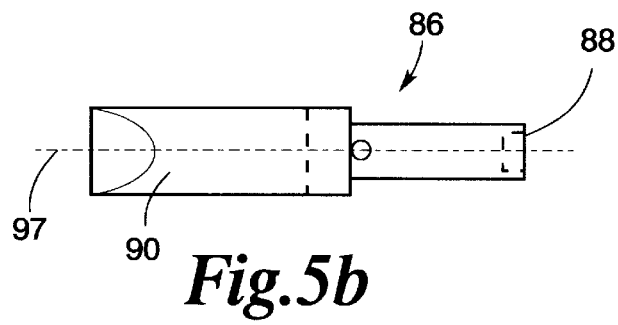
FIG. 5(b) is a plan view of the coupler of the plate probe of FIG. 4.
Figure 5C:
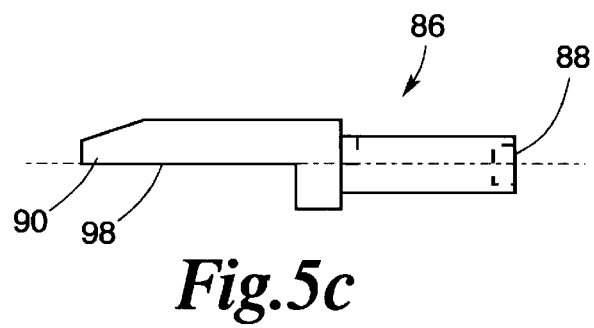
FIG. 5(c) is an elevation view of the coupler of the plate probe of FIG. 4.

The present invention is directed to a plate probe 82, shown in FIGS. 4 and 5, and to an associated system and method for guiding and verifying planar bone cuts. Such planar cuts, or osteotomies, are performed by attaching a cutting guide to the bone and inserting a saw blade into an opening, such as a slot, such as of the cutting guide. The plate probe 82 has a planar portion 92, which is configured so that it can be inserted into the cutting slot of the cutting guide, before inserting the saw blade to perform an osteotomy during arthroplastic surgery. The plate probe 82 is connected with a computer system which tracks the position and orientation of the planar portion 92 and permits an operator to adjust the cutting guide so that the osteotomy coincides with a planned position and orientation on the bone. The plate probe 82 may be used, for example, in a computer-aided arthroplastic system, such as the system disclosed in U.S. Pat. No. 6,002,859, which is incorporated herein by reference.

Figure 2:
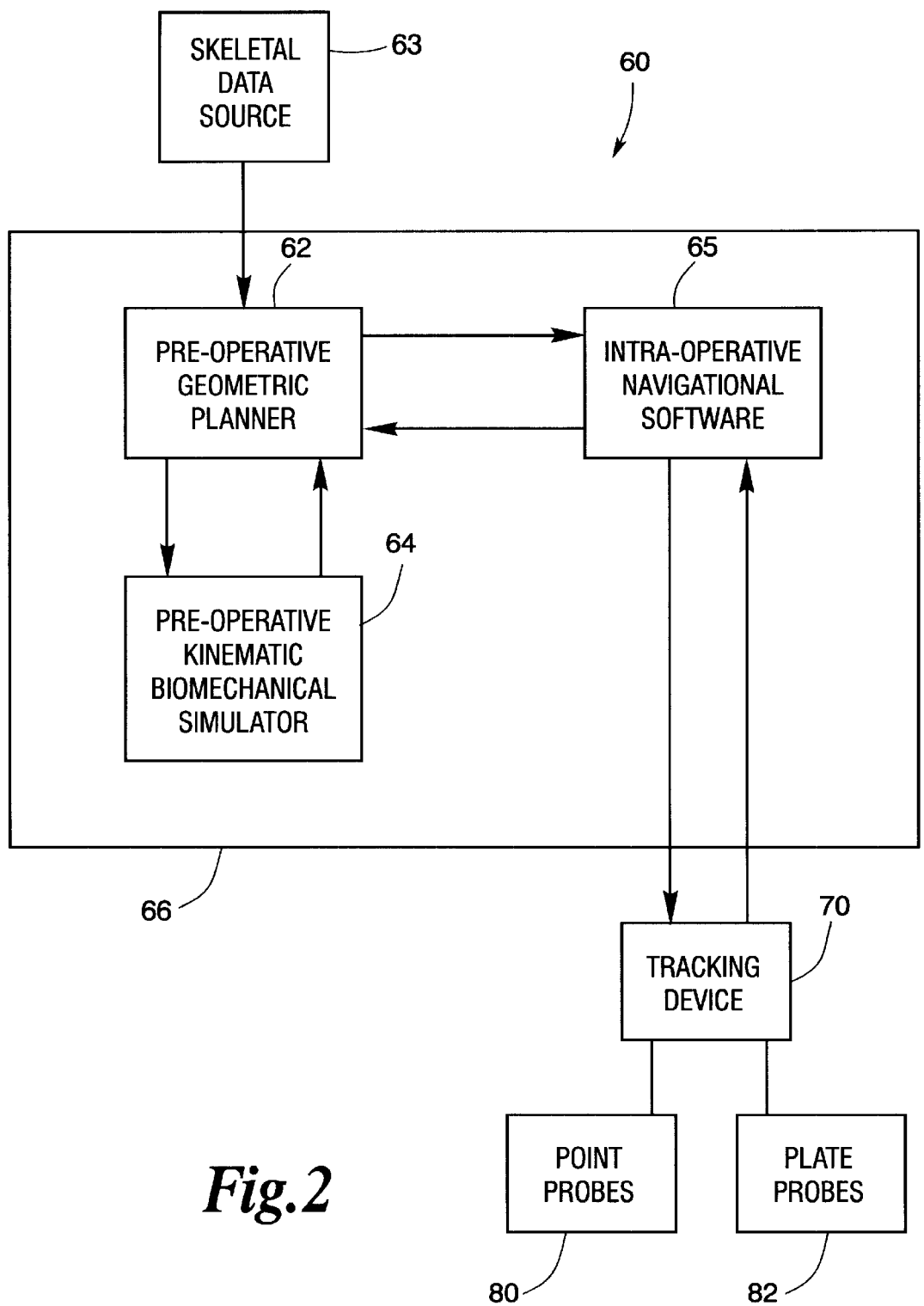
FIG. 2 is a system diagram incorporating an embodiment according to the invention.
Figure 3:
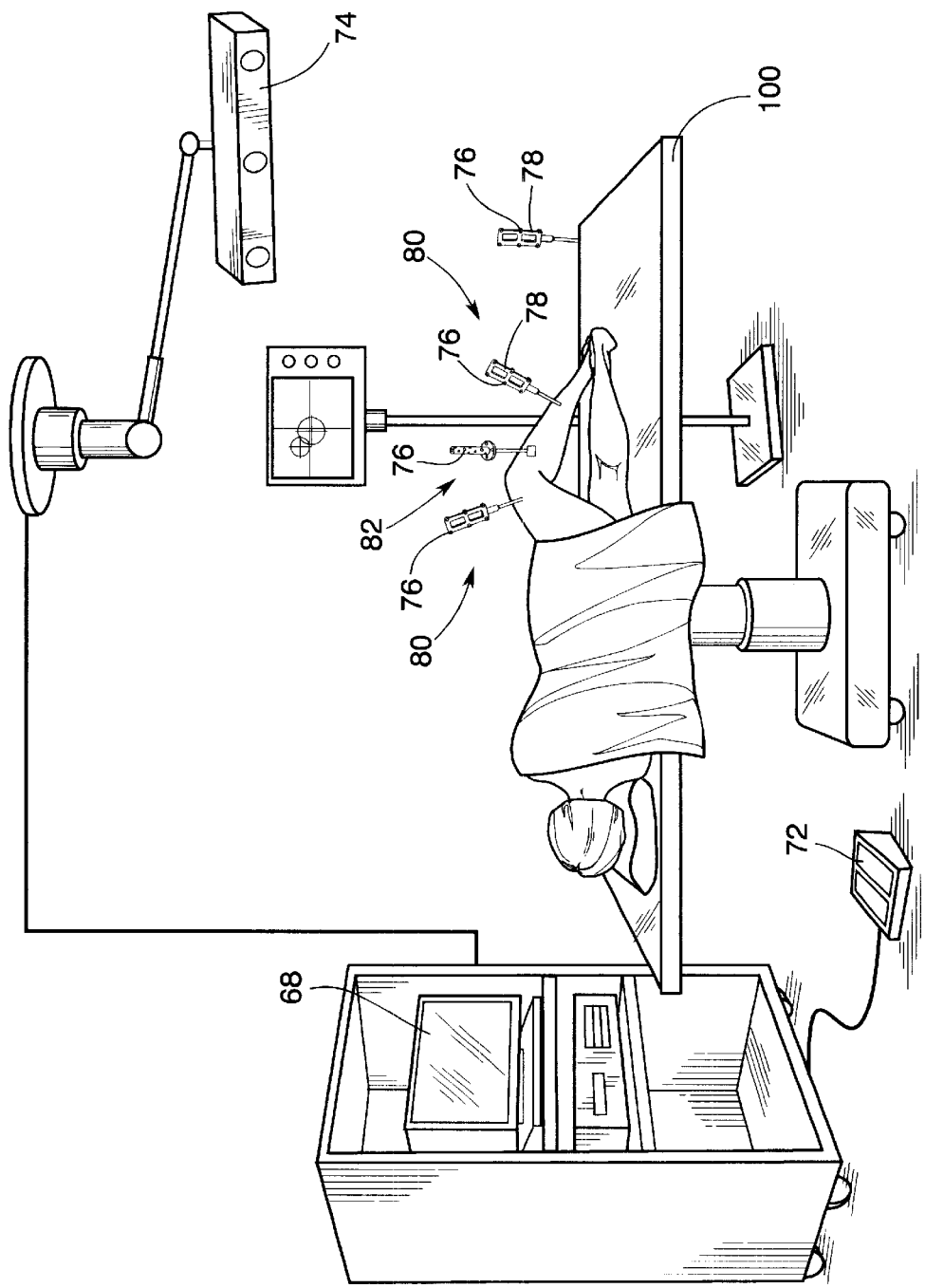
FIG. 3 is a schematic layout illustrating the use of the system of FIG. 2 in a knee replacement operation.

FIG. 2 schematically illustrates the plate probe in a system 60 for facilitating the implantation of artificial components during a surgical operation that requires an osteotomy. The system 60 incorporates the main modules described in U.S. Pat. No. 6,002,859 and includes the additional features of the present invention. The system 60 includes a preoperative geometric planner 62, which is used to create geometric models of the joint and the components to be implanted based on geometric data received from a skeletal structure data source 63. The geometric planner 62 is interfaced with a pre-operative kinematic biomechanical simulator 64 that simulates movement of the joint using the geometric models for use in determining implant positions, including angular orientations, for the components. The implant positions are used in conjunction with the geometric models in an intra-operative navigational software 65 to guide a medical practitioner in the placement of the implant components at the implant positions. The pre-operative geometric planner 62, the pre-operative kinematic biomechanical simulator 64 and the intra-operative navigational software 65 are implemented using a computer system 66 having at least one display monitor 68, as shown in FIG. 3. During the pre-operative stages of the method, the display monitor 68 is used for viewing and interactively creating and/or generating models in the pre-operative planner 62 and displaying the results of the biomechanical simulator 64. The pre-operative stages of the method may be carried out on a computer (not shown) remote from the surgical theater.

During the intra-operative stages of the method, the computer system 66 is used to display the relative locations of the objects being tracked with a tracking device 70. The medical practitioner preferably can control the operation of the computer system 66 during the procedure, such as through the use of a foot pedal controller 72 connected to the computer system 66. The tracking device 70 can employ any type of tracking method as may be known in the art, for example, emitter/detector systems including optic, acoustic or other wave forms, shape based recognition tracking algorithms, or video-based, mechanical, electro-magnetic and radio frequency (RF) systems. In a preferred embodiment, schematically shown in FIG. 3, the tracking device 70 is an optical tracking system that includes at least one position sensor or camera 74 that is attached to the computer system 66 and positioned to detect light emitted from a number of special light emitting diodes (LEDs), or targets 76 which can be mounted on position trackers 78. The position trackers 78 can be attached to bones, tools, and other objects in the operating room equipment to provide precision tracking of the objects. Some position trackers 78 are configured to receive point probes 80. The point probes 80 come in contact with a point and enable the tracking device to track the position of that point. To track the position of a plane for a planned osteotomy, adjust the plane of the cut and verify the cut, the plate probe 82, as described in further detail herein below, is connected to the tracking device 70.

The plate probe 82, includes a plate 84 and a coupler 86. The coupler 86 has a first end 88, which is configured to be coupled with a position tracker 78, and a second end 90 which is attached to the plate 84. The plate 84 includes the planar portion 92 and a handle portion 94. The planar portion 92 of the plate 84 is configured so that it can be inserted into the openings of a variety of cutting guides which are used to perform osteotomies during arthroplastic surgery, such as cutting slots 96, 102, 104 shown in FIGS. 6 and 12. The planar portion 92 has at least one and preferably two parallel (top and bottom) planar surfaces 22 and may be configured to include two longitudinal edges 93 and a transverse edge 91. The longitudinal edges 93 and the transverse edge are preferably straight so that the edges themselves can be used to test position and direction as well. The longitudinal edges 93 may be parallel to each other and the transverse edge 91 may be perpendicular to the longitudinal edges 93 so that the planar portion has a substantially rectangular shape, but other shapes may be used as desired. The planar portion 92 may also have a central longitudinal axis 95. The thickness of the planar portion 92 of the plate 84 should not be greater, and is preferably slightly less than the width of the cutting slots of the cutting guides, and the length of the transverse edge 91 should not be greater, and is preferably less than the length of the cutting slots, so that the planar portion can be easily inserted in the cutting slots. The plate 84 is made of a material that is substantially rigid so that the planar portion 92 remains flat and does not bend or flex while in use. The material could be any appropriate metal, plastic or polymer material.

The handle 94 of the plate 84 may have a substantially rectangular shape with a central longitudinal axis 97. The handle 94 is also made of material that is substantially rigid, such as a metal or rigid plastic or polymer, and is attached to the second end 90 of the coupler 86 in such way that the plate probe 82 is substantially rigid. For example, the handle may be welded or silver-soldered to a plate contact surface 98 of the coupler or may be formed as one integral piece by metal casting, when the plate probe 82 comprises a metallic material. A plastic plate probe 82 may also be formed as an integral piece by molding or injection molding. It will be appreciated that other modern techniques known in the art may also be used, such as laser-guided material deposition or sintering. The coupler 86 is attached to the handle 94 such that the handle 86 is centered about the handle axis 97. If the handle 94 and plate 84 are distinct units, they may also be attached to the plate 84 by any other means of attachment, known in the art. Care must be taken to avoid bending or flexing at the area of joinder, however, so that the planar surface 22 of the plate probe 82 does not deviate from the orientation registered by the tracking device, as explained in more detail below.

The longitudinal axis of 95 of the planar portion 92 may be collinear with or, alternatively, intersect the longitudinal axis 97 of the handle portion 94 at an angle α. The angle α is largely arbitrary, but it is preferably chosen to increase visibility of the targets 76 on the position tracker 78 along the lines of view from the position sensor 74, when an optical tracking system is used. An angle α of about 160° may be used, for example.

The first end 88 of the coupler 86 is configured so that it can be removably connected to a position tracker 78. The connection may be effected by using threaded ends, clamping devices, bolt and nut connections, or any other type of connection known in the art, which combines quick connect/disconnect capability and substantial rigidity. For determining the position of an object in relation to some fixed frame, such as, for example, the operation table 100, the position tracker 78 must include at least three LED targets 76. By tracking the position of the targets 76, the position of the position tracker 78 is determined, and therefore the position of the planar portion 92 of the plate probe 82 is also determined. The substantial rigidity of the plate probe 82 and the substantial rigid connection with the position tracker 78 enable the position sensor 74 to track the position of the plane of the planar portion 92 using principles of rigid body motion. A variety of tracking devices 70 and position sensors 74, including software and hardware, are offered by, for example, the Northern Digital Inc., Ontario, Canada, and from Polhemus Incorporated, Colchester, Vt. Position trackers may be obtained from Traxtal Technologies, Ontario, Canada. Although the plate probe 82 and its connection to the tracker 78 are preferably substantially rigid, a flexible or hinged probe 82 flexibly or hingingly connected to the tracker 78 may be used with tracking device systems that do not rely on rigidity to determine the position of tracked objects and include software that takes into account the flexibility of the tacked objects and their connections to the tracker.

The system 60 of FIG. 2 operates as follows. The skeletal structure of the joint and the associated bones are determined using tomographic or other data from the skeletal data source 63. The data may be obtained, for example, from computed tomography (CT), magnetic resonance imaging (MRI), positron emission tomographic (PET), or ultrasound scanning of the joint and surrounding structure, or other imaging techniques, most preferably techniques that provide three dimensional images, although imaging techniques are not required for the operation of the system 60. The data from the scanned structure generated by the skeletal data source 63 is provided to the geometric planner 62 for use in producing a model of the skeletal structure and geometric models of the artificial components to be implanted into the joint. The geometric models of the joint and the artificial components are used to perform biomechanical simulations of the movement of the joint containing the implanted artificial components in the pre-operative kinematic biomechanical simulator 64. The biomechanical simulations are preferably performed at a number of test positions to dynamically optimize the size, position and orientation of the artificial components in the patient's joint to achieve a predetermined range of motion following surgery. The predetermined range of motion for a particular patient is determined based on the expected activities of the patient following surgery. For example, with regard to hip and knee functions, daily activities including getting out of bed, walking, sitting and climbing stairs require different ranges of motion. The simulated movement of the joint at various implant positions is used in the computer 66 to calculate a range of motion for each implant position and to compare the calculated ranges of motion to the predetermined range of motion to select an implant position for the artificial components. A goal of the simulation process is to find the implant position which optimizes the calculated range of motion using the predetermined range of motion as a basis for optimization. The determination of the implant position can be further influenced by other factors such as the variation in the calculated range of motion as a function of implant component orientation. This criterion is useful for determining the surgical margin of error that is available to the medical practitioner without a substantial diminution in the range of motion of the joint.

In the operating theater, the joint model based on the skeletal data is aligned with the intra-operative position of the patient's joint using, for example, a technique known as three dimensional (3D) surface registration, which is described in more detail in U.S. Pat. No. 6,002,859. In 3D surface registration, the intra-operative position of the patient's joint can be tracked using the joint model by obtaining positional data from a point on the joint that provides spatial correspondence between the pre-operative models and the intra-operative measurements.

The position of the joint and the implant components are tracked and compared in near real time to the implant position identified in the joint model. The tracking device 70 provides the positional data representative of the position of the patient's joint to the computer system 66. The computer system 66 employs registration routines within the intra-operative navigational software 65 to determine the position and orientation of the joint and then displays the relative positions of the artificial component and the implant position. The tracking device 70 can also be used to track and provide positional data representative of the position of other physical objects in the operating room, such as surgical instruments, point probes 80 and plate probes 82. The point probes 80 can provide information about discrete points to which they are attached. In contrast, the plate probes 82 may provide information about the position and orientation of planes to which they are aligned, and are used to track, align and verify planar osteotomies during arthroplastic surgery.

Figure 6:
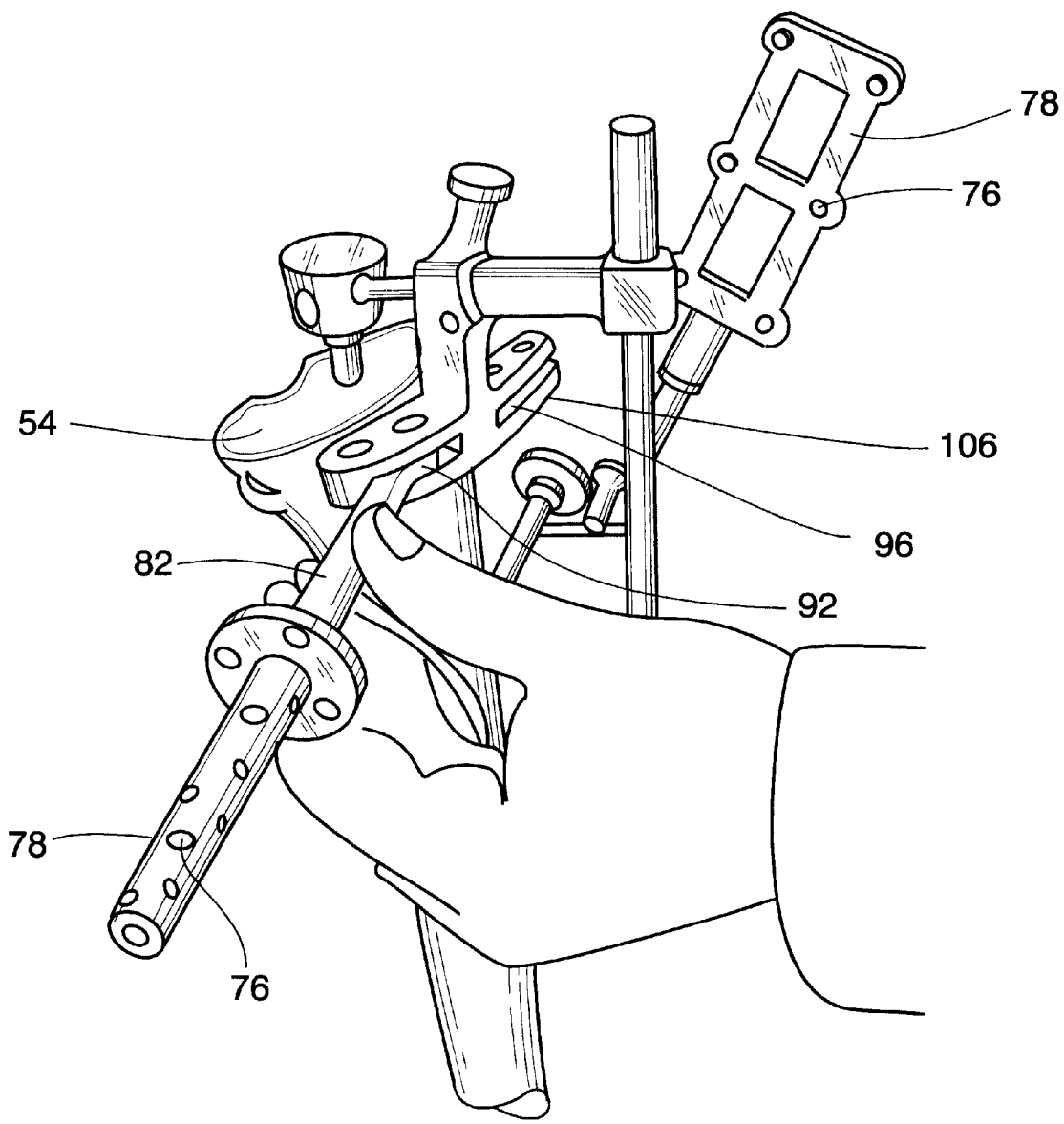
FIG. 6 is a schematic view of the plate probe of FIG. 4 inserted into the cutting slot of a tibial cutting guide.
Figure 7:
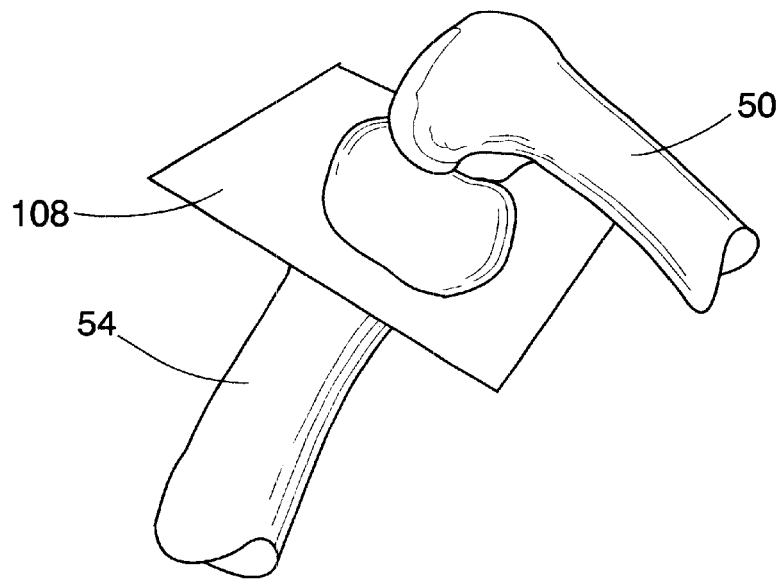
FIG. 7 is a schematic of a computer screen showing the cut position of the tibia.
Figure 8:
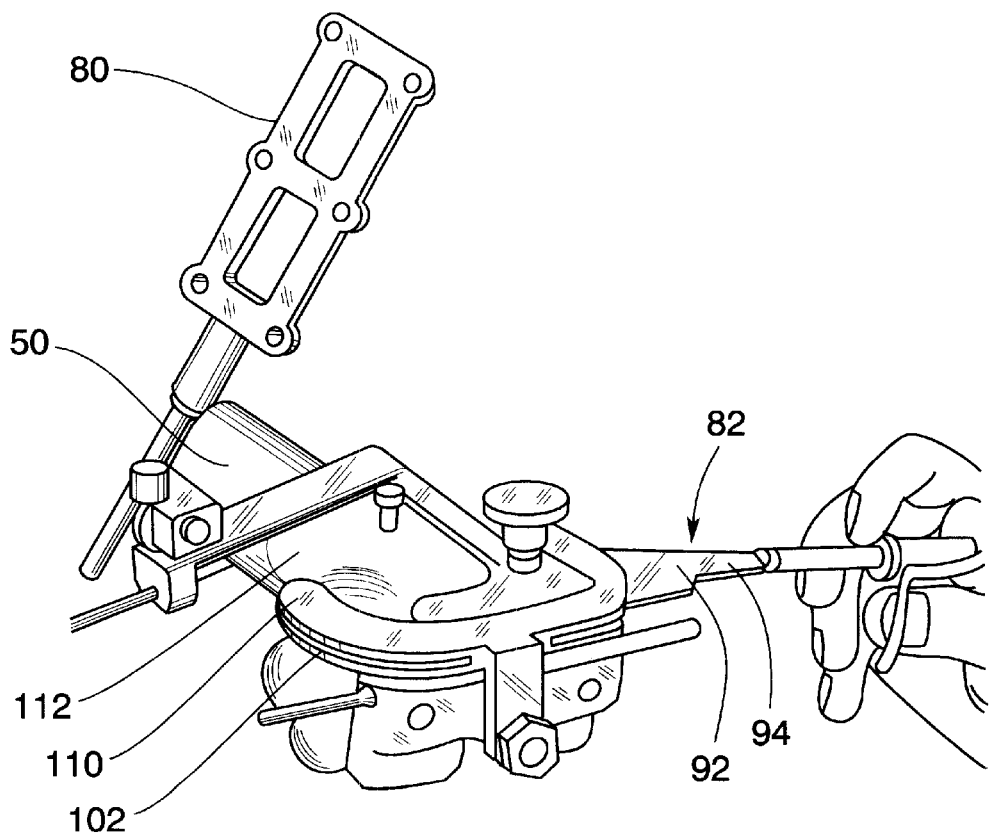
FIG. 8 is a schematic view of the plate probe of FIG. 4 inserted into the cutting slot of an anterior femoral cutting guide.
Figure 9:
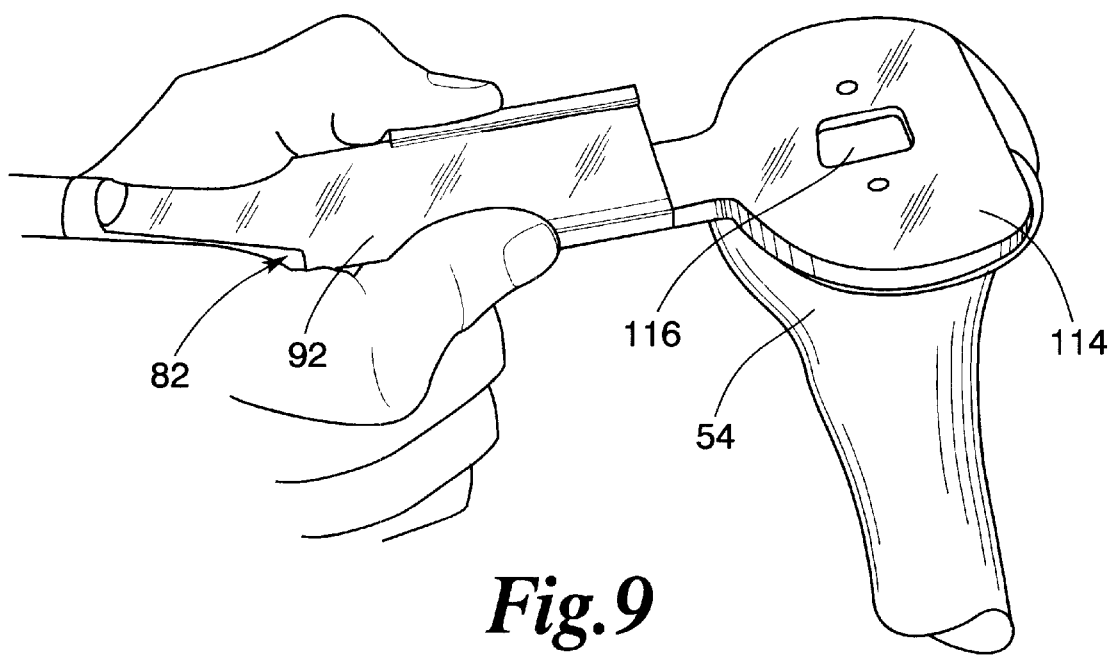
FIG. 9 is a schematic view of the plate probe of FIG. 4 used in association with a tibial stem template.
Figure 10:
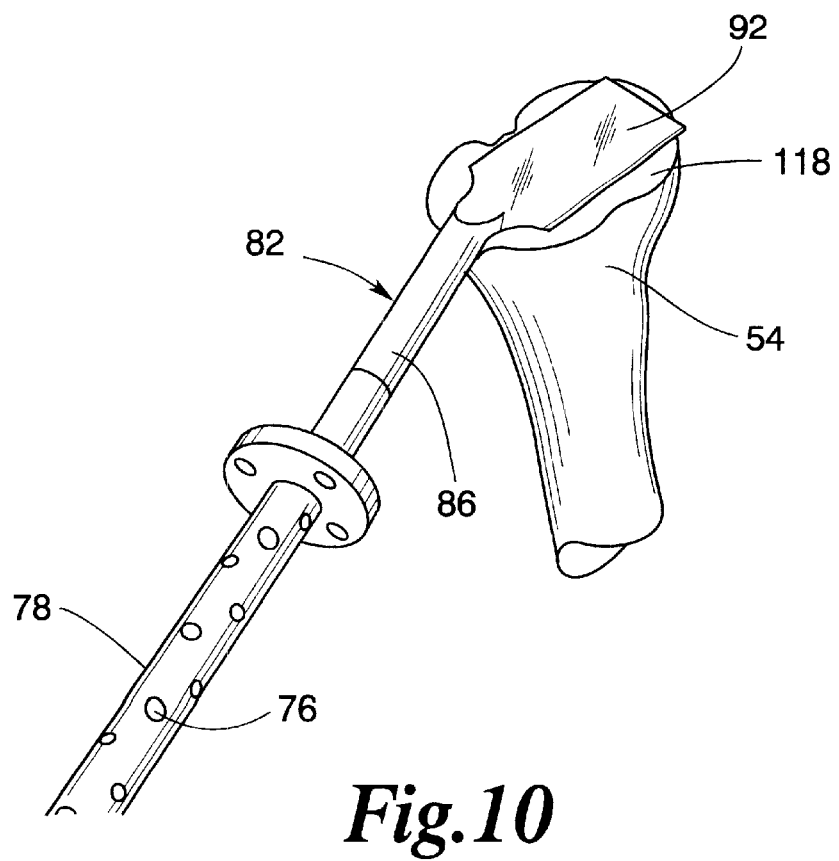
FIG. 10 is a schematic view of the plate probe of FIG. 4 used to verify a tibial cut.

FIGS. 6–11 present exemplary uses of the plate probe 82 in the context of a TKR. In FIG. 6 the planar portion 92 of the plate probe 82 is inserted into the cutting slot 96 of a tibial cutting guide 106 to adjust the alignment of the guide prior to cutting the upper surface of the tibia 54. The adjustment is accomplished by tracking the planar portion 92 and adjusting its position so that the image of the plane 108 defined by the planar portion 92 coincides with the plane of the planned cut of the tibia 54, as shown in FIG. 7, on the computer screen 68. After the adjustment is made, the plate probe 82 is removed and the blade of a saw is inserted into the cutting slot 96 to cut the top of the tibia 54. The tibial cutting guide 106 is then removed and the plate probe 82 is placed on the tibial cut surface 118 to verify its orientation, as shown in FIG. 10. If any corrections are required, the procedure is repeated.

FIG. 8 illustrates the use of the plate probe 82 to adjust an anterior femoral cutting guide 110 prior to cutting the anterior femoral condyles 112 through the slots 102 with the blade of a reciprocating saw. The planar portion 92 of the plate probe 82 is inserted into the slot 102 and the anterior femoral cutting guide 110 is adjusted until the image of the plane defined by the planar portion 92 coincides with the plane of the planned cut of the femoral condyles 112, as shown on the computer screen 68. After the adjustment is made, the plate probe 82 is removed and the blade of a saw is inserted into the cutting slots 102 to cut the anterior condyles 112. The anterior cutting guide 110 is then removed and the plate probe 82 is placed on the cut surface to verify its orientation. If any corrections are required, the procedure is repeated.

FIG. 9 illustrates the use of the plate probe 82 to adjust the rotational orientation of a tibial stem template prior to cutting the tibial stem hole 116 for inserting a tibial component 58. See also FIG. 1.

Figure 11A:
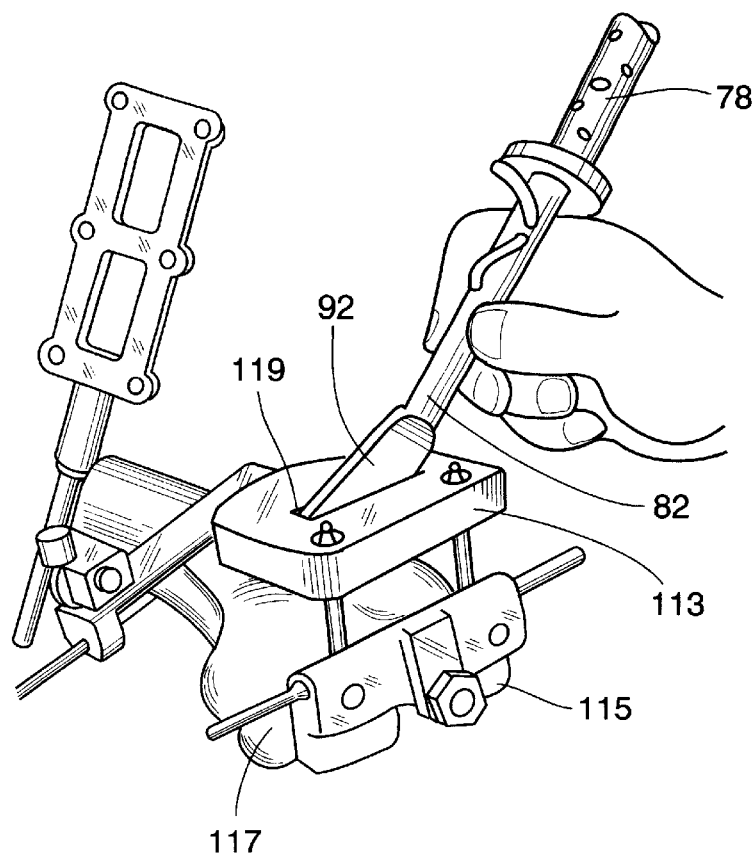
FIG. 11(a) a schematic view of the plate probe of FIG. 4 inserted into the cutting slot of a distal femoral cutting guide.
Figure 11B:
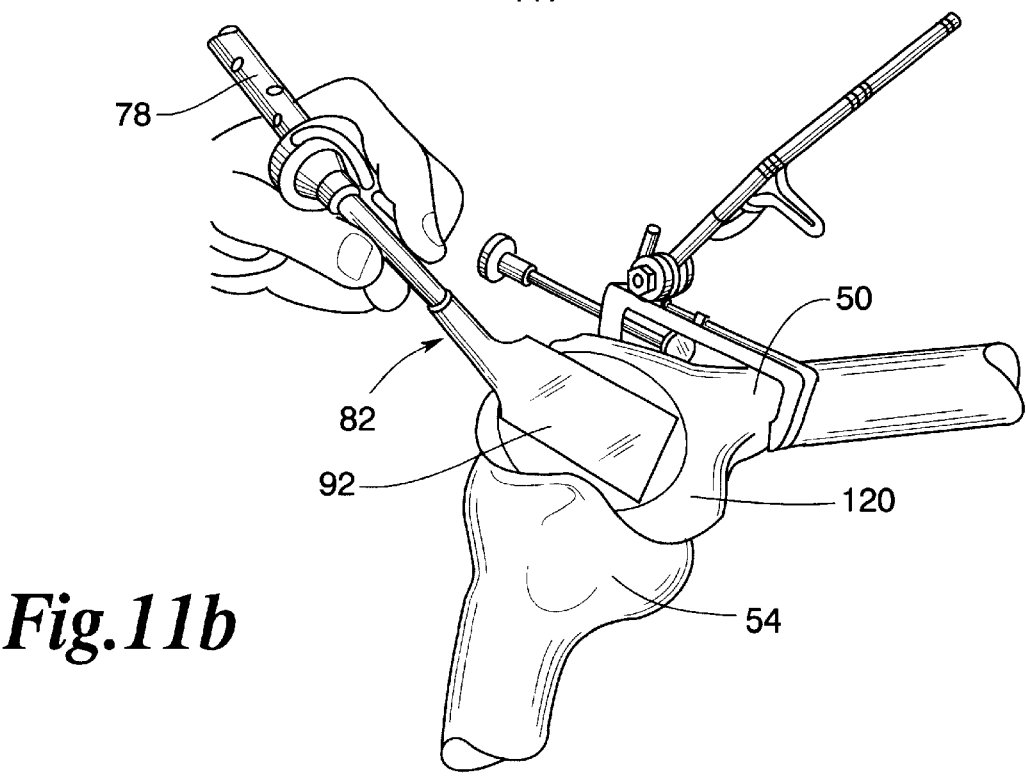
FIG. 11(b) is a schematic view of the plate probe of FIG. 4 used to verify a distal femoral cut.

FIG. 11(a) illustrates the use of the plate probe 82 to adjust a distal femoral cutting guide 113 in relation to a femoral intramedullar alignment guide 115 prior to cutting the distal femur 117. The planar portion 92 of the plate probe 82 is inserted into the cutting slot 119 of the distal femoral cutting guide 113 to determine the alignment of the planned cut. After the distal femoral cutting guide 113 is adjusted, the plate probe 82 is removed and the distal femur 117 is cut with a saw blade, which is inserted into the cutting slot 119. After the osteotomy, the orientation of the distal femoral cut surface 120 is verified by placing the planar portion 92 of the plate probe 82 on the cut surface 120, as shown in FIG. 11(b). If any corrections are needed, the procedure is repeated.

Figure 12A:
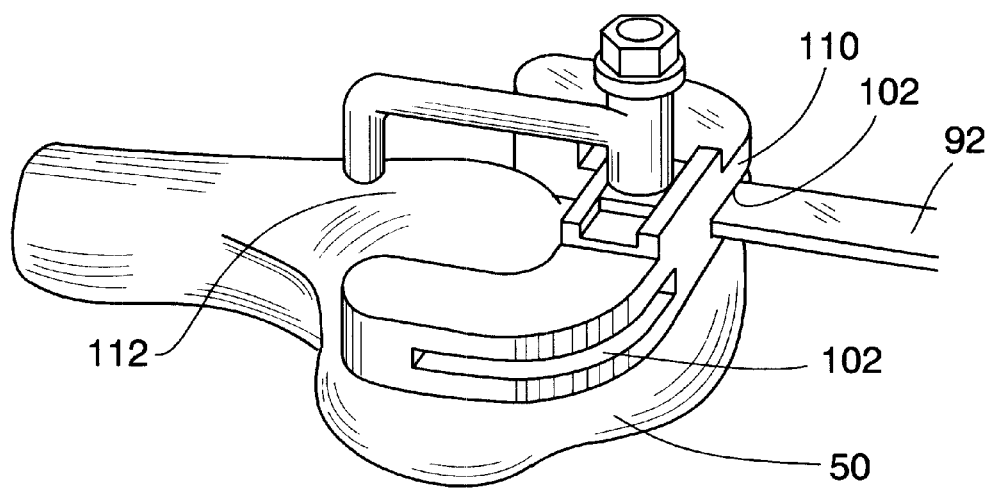
FIG. 12(a) is a perspective view of an anterior femoral cutting guide showing the plate probe in the cutting slot.
Figure 12B:
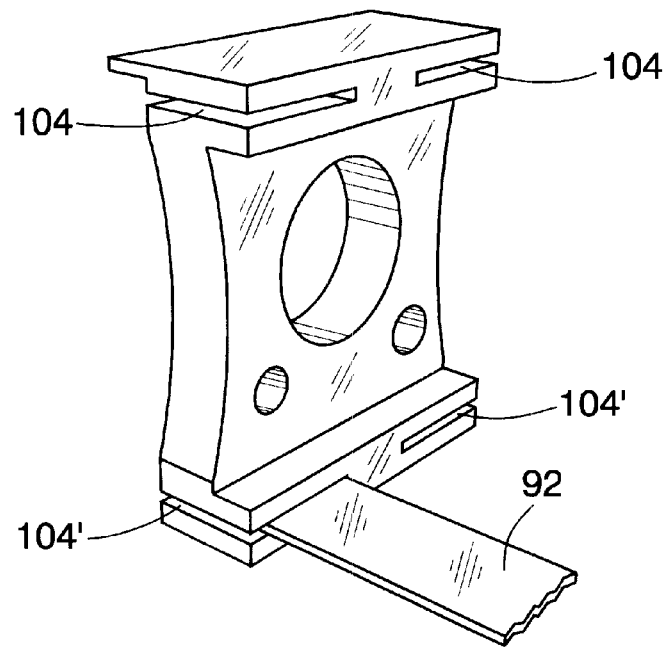
FIG. 12(b) is a perspective view of a femoral anterior/posterior cutting guide showing the plate probe in the cutting slot.

FIG. 12(a) show in greater detail the anterior femoral cutting guide 110 of FIG. 8. FIG. 12(b) shows a femoral anterior/posterior cutting guide, which, in this example, has two sets of cutting slots 104, 104' for cutting the anterior and posterior condyles of the femur. The planar portion 92 of the plate probe 82 may be used to adjust and verify planar cuts in connection with either set of slots 104, 104'.

It will be appreciated that the description of the invention in connection with procedures and devices associated with a TKR is merely exemplary, and the plate probe, system and methods of the present invention can be used in any arthroplastic surgery in which a planar osteotomy is required. The present invention facilitates tracking the plane of any osteotomy, such as, but not limited to, a tibial cut 118 or a femoral cut 120, by means of the plate probe 82 and obtaining orientational data, adjusting and aligning the osteotomy by comparison to a computer model of the plane of the osteotomy 108 on a computer screen 68, as shown for example in FIG. 7, and verifying the plane of the osteotomy post-operatively as shown, for example, in FIGS. 10 and 11.

Whereas particular embodiments of the invention have been described herein for the purpose of illustrating the invention and not for the purpose of limiting the same, it will be appreciated by those of ordinary skill in the art that numerous variations of the details, materials and arrangement of parts may be made within the principle and scope of the invention without departing from the invention as described in the appended claims.

What is claimed is:

1. A probe for facilitating the orientation of an osteotomy, the probe comprising:
    a coupler having a first end and a second end, the first end configured to be operatively coupled in use with a position tracker; and
    a plate configured to be insertable in use into an opening of a bone-cutting guide, the opening defining the orientation of the osteotomy, wherein the plate is structurally attached to the coupler such that the orientation of the plate is determinable in reference to the position tracker, wherein the plate has a planar portion and a handle portion, the planar portion being configured to be insertable in use into the bone-cutting guide and being coplanar with the handle portion, and wherein the planar portion and the handle portion each have a longitudinal axis and the axes are at an angle relative to each other.

2. The probe of claim 1, wherein the plate is fixedly attached to the coupler such that the probe is substantially rigid.

3. The probe of claim 1, wherein the plate is integrally connected to the coupler.

4. The probe of claim 1, wherein the position tracker is in communication with a computer.

5. The probe of claim 1, wherein the handle portion is attached to the second end of the coupler.

6. The probe of claim 1, wherein the angle is selected to maximize visibility of the position tracker from an optical tracking device.

7. The probe of claim 1, wherein the planar portion includes at least one planar surface, two longitudinal edges and a distal transverse edge.

8. The probe of claim 7, wherein the planar portion has two substantially parallel planar surfaces, one on each side thereof.

9. The probe of claim 7, wherein the longitudinal edges are substantially parallel to each other.

10. A probe apparatus for facilitating the orientation of an osteotomy, the apparatus comprising:
   a position tracker; and
   a plate having a planar portion, a handle portion and a coupling portion coupled to the position tracker, such that the probe apparatus is substantially rigid and the planar orientation of the plate is determinable in reference to the position tracker, wherein the planar portion is configured to be insertable in use into a bone-cutting guide and is coplanar with the handle portion, wherein the handle portion and the planar portion each have a longitudinal axis and the axes are at an angle relative to each other.

11. A probe apparatus for facilitating the orientation of an osteotomy, the apparatus comprising:
   a plate having a planar portion and a handle portion, the planar portion being configured to be insertable in use into a bone-cutting guide and being coplanar with the handle portion, wherein the handle portion and the planar portion each have a longitudinal axis and the axes are at an angle relative to each other; and
   a position tracker coupled to the plate such that the probe apparatus is substantially rigid and the orientation of the plate is determinable in reference to the position tracker.

12. A system for tracking and verifying the orientation of planar cuts in bone during surgery, the system comprising:
   a computer navigation system;
   a position tracker in operative communication with the computer navigation system; and
   a probe operatively connected with the position tracker, the probe comprising:
      a plate having a planar portion integral with a handle portion, wherein the planar portion is structurally configured to be insertable in use into an opening in a bone-cutting guide, the opening defining the orientation of one of said planar cuts in bone; and
      a coupler having a first end and a second end, the first end configured to be operatively connected to the position tracker and the second end structurally configured for attachment to the handle portion such that the planar orientation of the plate relative to a reference is determinable through the position tracker.

13. The system of claim 12 wherein the position of the planar portion relative to a reference is determinable through the position tracker.

14. A system for facilitating the implantation of an artificial component in a joint during arthroplastic surgery requiring an osteotomy, the system comprising:
   a computer system including:
      a pre-operative geometric planner; and
      a pre-operative kinematic biomechanical simulator in communication with the preoperative geometric planner wherein the pre-operative kinematic biomechanical simulator outputs a position for implantation of the artificial component and a position and orientation for the osteotomy;
   a position tracker in communication with the computer system through an intra-operative navigational module; and
   a probe comprising a coupler and a plate, wherein the coupler is configured to be connected to the position tracker such that position and orientation of the plate are determinable from the position and orientation of the tracker, and wherein the plate is configured to be insertable into a bone-cutting guide.

15. An apparatus for facilitating an osteotomy procedure in preparation for the implantation of an artificial component in a joint using a bone-cutting guide, the apparatus comprising:
   a tracking device configured to collect positional and orientational tracking data;
   a probe comprising a coupler and a plate, wherein the coupler is configured to be connected to the tracking device such that position and planar orientation of the plate are tracked, and wherein the plate is configured to be insertable into the bone-cutting guide;
   a computer system in communication with the tracking device comprising,
      means for creating a joint model of the joint;
      means for creating a component model of the component;
      means for simulating movement of the joint with the artificial component in a test position using the component model and the joint model;
      means for calculating a range of motion of the joint for the test position based on the simulated movement;
      means for determining an implant position of the component based on a predetermined range of motion and the calculated range of motion;
      means for identifying the determined implant position in the joint model;
      means for aligning the joint model with the joint and the artificial component model with the component based on the positional tracking data; and
      means for aligning an osteotomy plane based on the orientation tracking data of the plate of the probe.

16. A method for facilitating the implantation of an artificial component in a joint during arthroplastic surgery that requires a planar osteotomy, the method comprising:
   creating a model of the joint and a model of the artificial component;
   calculating a range of motion based on a simulated movement of the joint with the artificial component in a test position;
   determining the implant position based on the calculated range of motion and a predetermined range of motion;
   aligning said model of the joint with the joint and the model of the artificial component with the artificial component;
   tracking the artificial component and the joint;
   modeling the plane of the osteotomy; and
   tracking the plane of the osteotomy.

17. A method of facilitating a planar osteotomy on a joint during computer-aided arthroplastic surgery, the method comprising:

positioning a bone-cutting guide having an opening therein, on a portion of the joint prior to the osteotomy;

attaching a probe having a planar portion to a position tracker;

inserting the planar portion into the opening in the bone-cutting guide;

tracking the plane of the planar portion; and verifying the orientation of the plane of the osteotomy before performing the osteotomy.

18. The method of claim 17, wherein verifying the orientation of the plane of the osteotomy further comprises correcting the orientation of the plane of the osteotomy.

19. The method of claim 17 further comprising:

verifying the orientation of the plane, of the osteotomy after performing the osteotomy.

20. A system comprising:

a computer system comprising:

a surgical navigation module;

a pre-operative geometric planner; and a pre-operative kinematic biomechanical simulator in communication with the preoperative geometric planner wherein the pre-operative kinematic biomechanical simulator outputs a position for implantation of an artificial component and a position and orientation for the osteotomy;

a position tracker in operative communication with the computer system; and a probe comprising a planar portion, wherein the probe is removably connected to the position tracker such that the position and orientation of the planar portion are determinable, and wherein the planar portion is configured to be insertable in use into an opening in a cutting guide for an osteotomy during arthroplastic surgery.

* * * * *

UNITED STATES PATENT AND TRADEMARK OFFICE
CERTIFICATE OF CORRECTION

PATENT NO. : 6,514,259 B2  
DATED : February 4, 2003  
INVENTOR(S) : Picard et al.

It is certified that error appears in the above-identified patent and that said Letters Patent is hereby corrected as shown below:

<u>Title page,</u>  
Item [54], Title, delete "ARTHOPLASTY" and replace therewith  
-- ARTHROPLASTY --.

Signed and Sealed this

Tenth Day of June, 2003

JAMES E. ROGAN  
*Director of the United States Patent and Trademark Office*